(12) United States Patent
Henderson

(10) Patent No.: US 7,326,895 B1
(45) Date of Patent: Feb. 5, 2008

(54) SPLATTER LID

(76) Inventor: Bradley J. Henderson, 3910 N. Fremont Dr., Unit F, Chicago, IL (US) 60613

( * ) Notice: Subject to any disclaimer, the term of this patent is extended or adjusted under 35 U.S.C. 154(b) by 0 days.

(21) Appl. No.: 11/564,143

(22) Filed: Nov. 28, 2006

(51) Int. Cl.
*H05B 6/80* (2006.01)

(52) U.S. Cl. ............... 219/735; 219/729; 219/731; 219/732; 219/734; 219/735; 220/252

(58) Field of Classification Search ........ 219/728–735, 219/756, 757, 762, 763; 426/107, 234, 241–243; 99/DIG. 14; 220/4.22, 213, 252
See application file for complete search history.

(56) References Cited

U.S. PATENT DOCUMENTS

| | | | |
|---|---|---|---|
| 2,428,839 A * | 10/1947 | Di Salino | ........... 220/252 |
| 2,687,026 A | 8/1954 | Gleason | |
| 4,801,773 A | 1/1989 | Hanlon | |
| 5,028,754 A | 7/1991 | Chiba | |
| 5,550,356 A | 8/1996 | Tripp et al. | |
| 5,801,363 A | 9/1998 | Michaluk, III | |
| D416,436 S | 11/1999 | Miller | |

\* cited by examiner

*Primary Examiner*—Tu Ba Hoang
*Assistant Examiner*—Leonid Fastovsky
(74) *Attorney, Agent, or Firm*—Advantia Law Group; Michael W. Starkweather; Jason P. Webb

(57) ABSTRACT

A spatter guard for covering food in an oven. The guard includes: a first shell configured to cover food, having: a first semi-hemispherical barrier member with a plurality of apertures therein. Additionally, there is a second shell is pivotally coupled to the first shell to substantially form a hemispherical barrier and an array of substantially parallel semi-hemispherical barriers. The array includes a second semi-hemispherical barrier member with a plurality of apertures therein. Moreover, the first shell has a plurality of protrusions extending downwardly from a bottom of the first hemispherical barrier member to space the first shell from a surface. Further, there is a flange that extends outwardly from a bottom of the first hemispherical barrier member. Further, the second shell has a protrusion extending outwardly therefrom and is configured to be used as a handle for actuating the second shell between the first and second positions.

11 Claims, 1 Drawing Sheet

SPLATTER LID

BACKGROUND OF THE INVENTION

1. Field of the Invention

The present invention relates to apparatus for covering food items while cooking, specifically, a splatter guard for covering food in an oven or the like.

2. Description of the Related Art

In the related art, it has been known to use devices to shield food while cooking the food in a certain types of ovens. Food of various types is often cooked in microwave ovens. When such food is not completely enclosed by a container there is a great chance that spilling, splattering and splashing of food particles will occur. When such disturbances of the food due to the heating process occurs the interior of the microwave oven will need to be cleaned. Effort and time must necessarily be expended every time the microwave is cleaned. The greater the frequency of spills the greater the need to clean the microwave oven. Therefore there is need for a device which helps prevent spilling, splattering, and splashing of food from contaminating the interior of a microwave oven. A device which is convenient, easy to use, and effectively keeps the microwave clean. Some improvements have been made in the field. Examples include but are not limited to the references described below, which references are incorporated by reference herein:

U.S. Pat. No. 5,801,363, issued to Michaluk, discloses a microwave oven with built-in food covering mechanism, the microwave having a body defined by a top, bottom, sides and rear. A door is hingedly connected to the body and is opened to reveal an open interior of the body. A covering member is suspended within the oven interior and is operably connected to an electric motor built into the microwave body. The motor includes a rotating gear head which rotates in one of two directions to either wind or unwind the cord to either elevate or lower the covering member within the interior. A microprocessor energizes and deenergizes the motor and is operated by any of a selection of spring loaded, pressure actuated or sensing switch assemblies within the microwave interior.

U.S. Pat. No. 2,687,026, issued to Gleason, discloses a dish cover.

U.S. Pat. No. 5,550,356, issued to Tripp et al., discloses a food covering device for use with a microwave oven. The microwave oven has a door hingedly attached thereto and an interior which is defined by a top, sides and a bottom. The device includes a cover having a top and side wall which defines an open interior. The cover is suspended within the oven enclosure by a cord which attaches to the cover at one end and to the door of the oven at the other end. The cover is actuated from a first suspended position within the oven enclosure to a second position overlaying the bottom of the oven enclosure when the door is closed. A height adjuster is provided for adjusting the extent which the cover is actuated from the first to the second position. The cover overlays an item of food placed upon the bottom of the microwave interior when it is desirable to heat the item. The cover may also be adjusted solely at the height adjuster without the opening and closing motion of the door.

U.S. Pat. No. 5,028,754, issued to Chiba, discloses a cooking hood used in making a cake in a microwave oven has a peripheral wall and a top wall formed with a center hole similar in shape to the top wall itself and is adapted to be put over a cake mold containing dough for a cake. The cake mold containing the dough and covered with the hood is put in a microwave oven to heat the dough to form a cake. The center hole is of such a size that the steam rising from the dough being heated will be released gradually through the hole so that the cake will be baked uniformly from the inside to the outside. The dough is made by kneading whipped egg, sugar, sifted flour, a fat such as margarine and water or milk with a whipper. The content of the water or milk should be larger by about 20 percent than when baking a cake of the same size in a gas or electric oven. The weight ratio of the water or milk to the flour should be about 55 percent.

U.S. Pat. No. 4,801,773, issued to Hanlon, discloses a protective cover for a dish being heated in a microwave oven is formed of moisture-absorbent, microwave transparent material forming a top member and an encircling wall member depending downwardly from the periphery of the top member to completely cover the dish to protect the interior of the oven from any possible spattering of food particles during the heating. The cover is formed of absorbent material so that any escaping fluids and food particles may be captured or absorbed by the cover. The wall member is fluted to give the cover self-supporting rigidity, and an upper edge of each fluted portion coincides with a scalloped portion of the top member. The cover may be treated with a microwave safe resin to increase the rigidity of the cover.

U.S. Design Pat. No. 416,436, issued to, discloses the ornamental design for a microwave plate cover.

The inventions heretofore known suffer from a number of disadvantages which include, complex, limited in use, limited adaptability, expensive, non-durable and/or fails to conveniently, effectively, and/or safely prevent contamination of the interior of microwave ovens.

What is needed is a splatter guard that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available splatter guards. Accordingly, the present invention has been developed to provide a splatter guard for covering food in an oven or the like.

There is one embodiment of a spatter guard for covering food in an oven that may include: a first shell that may be configured to cover food, and may have: a first semi-hemispherical barrier member; and/or a first plurality of apertures that may be through the first semi-hemispherical barrier member; and/or a second shell that may be pivotally coupled to the first shell. The first and/or second shells together may substantially form a hemispherical barrier when in a first position and/or form an array of substantially parallel semi-hemispherical barriers when in a second position. The array may further include: a second semi-hemispherical barrier member; and/or a second plurality of apertures that may be through the second semi-hemispherical barrier member.

According to one embodiment, the first shell may further includes a plurality of protrusions that may extend downwardly from a bottom of the first hemispherical barrier member and/or may be configured to space the first shell from a surface when in use.

In another embodiment, the first shell may have a flange extending outwardly from a bottom of the first hemispherical barrier member.

In yet another embodiment, the second shell may include a protrusion that may extend outwardly from a front of the second shell and/or may be configured to be used as a handle for actuating the second shell between the first and/or second positions.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
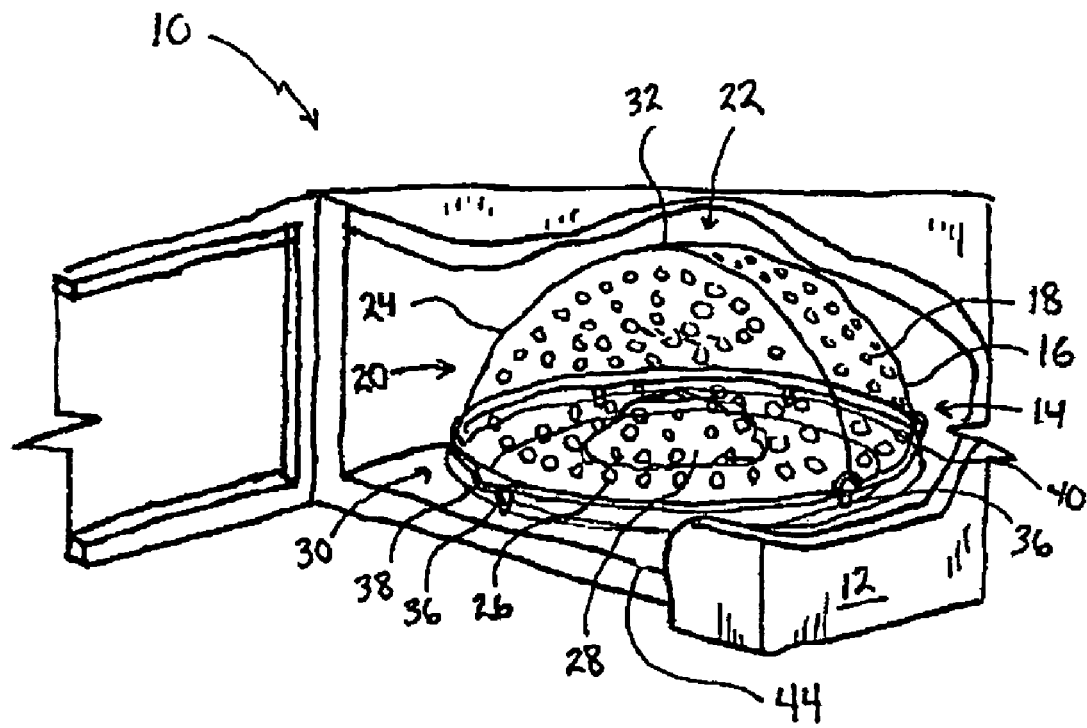
FIG. 1 is a cutaway perspective view of a splatter guard, according to one embodiment.
Figure 2:
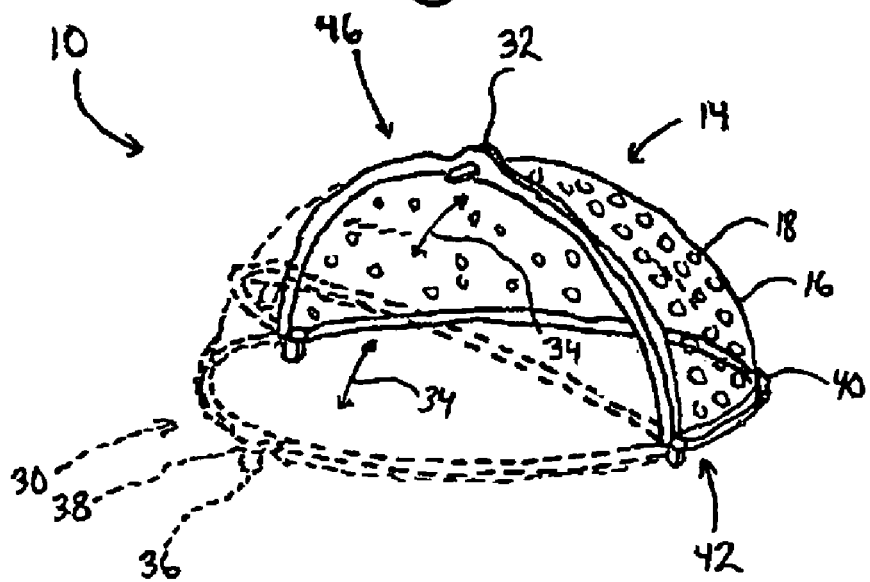
FIG. 2 is a perspective view of a splatter guard, according to one embodiment.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to "one embodiment," "an embodiment," or similar language means that a particular feature, structure, or characteristic described in connection with the embodiment is included in at least one embodiment of the present invention. Thus, appearances of the phrases "one embodiment," "an embodiment," and similar language throughout this specification may, but do not necessarily, all refer to the same embodiment, different embodiments, or component parts of the same or different illustrated invention. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the invention as claimed.

Each statement of an embodiment is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The independent embodiments are considered to be able to be combined in whole or in part one with another as the claims and/or art may direct, either directly or indirectly, implicitly or explicitly.

Finally, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

As used herein, "comprising," "including," "containing," "is, are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

Referring to the drawing figures, there is one embodiment of a spatter guard 10 for covering food 28 in an oven 12. A non-limiting example of such an oven is described in U.S. Pat. No. 7,109,454, issued to Lee, which is incorporated by reference herein. The guard, as shown, includes: a first transparent shell 14 configured to cover food, having: a first semi-hemispherical barrier member 16 with a first plurality of apertures 18 therein; and a second transparent shell 20 pivotally coupled to the first shell, having a second semi-hemispherical barrier 24 with a second plurality of apertures 26 therein.

The first shell 14 and second shell 20 cooperate together to substantially form a transparent hemispherical barrier 22 (also referred to as a dome) when in a first position 30 and an array 46 of substantially parallel semi-hemispherical barriers 16, 24 when in a second position 32. The transparency of the splatter lid 10 enables a user to visually monitor the lid preventing food 28 from splattering in the oven 12 while cooking. The splatter guard is structured to prevent the following non-limiting examples of food from splattering in the oven: meats, vegetables, starches, etc.

According to one embodiment of the present invention, the first shell 14 further includes a plurality of protrusions 36 extending downwardly from a bottom 42 of the hemispherical barrier members 16, 24 and is configured to space the first shell from a surface 44 when in use. The protrusions 36 coupled with the apertures 18, 26 in the barrier members serve as a medium for warm air inside of the insulated dome to ventilate therethrough in order to achieve thermal equilibrium with the ambient air inside of the oven 12.

In another embodiment of the present invention, the first shell has a flange 40 extending outwardly from the bottom 42 of the first hemispherical barrier member. The flange enables the leading edge of shell 20 to rest on shell 14 and facilitates sufficient distribution of weight of the shells when a user opts to open the hemispherical barrier 22. This keeping the array 46 of substantially parallel semi-spherical barrier members balanced when the shell 20 is in the second position 32.

In yet another embodiment of the present invention, the front of the second shell 20 includes a protrusion 38 extends outwardly therefrom, and is configured to be used as a handle for a user to actuate the second shell between the first position 30 and 32 second positions, thereby enabling a user to place a suitable covering over food 28 being cooked therein.

In operation, a user places the hemispherical dome 22 over food 28 cooking in an oven 12 to prevent the high temperature food and associated liquids from splattering on the interior walls of the oven. The user may place a bowl or plate of food into the oven and position the splatter lid 10 thereon, with shell 20 in the first position 30 to form a dome 22 over the food. While the food is cooking, the diameter of apertures 18, 26 in the dome 22 are sized to prevent food from flowing therethrough, and enable the release of warm air therethrough, thereby causing the air pressure inside of the dome to be in equilibrium with the air pressure inside of the oven. This thermal equilibrium prevents deformation of the dome 22, thereby protecting the lid 10 from melting or damage due to excessive heat. After use, the user then can grab the protrusion 36 with his or her hand in order to actuate the shell 20 upward from the first position 30 to the second position 32, as indicated by arrow 34, thereby forming an array 46 of substantially parallel semi-hemispherical barrier members 16, 24. This allows the user to retrieve the food from the oven without having to remove the lid from the oven.

Assuming the user keeps the lid in the oven 12 after use and desires to cook food again, the user may put food 28 into the oven and grab the protrusion 36 with his or her hand in order to actuate the shell 20 downward from the second position 32 to the first position 30, as indicated by arrow 34, thereby forming the dome 22. The user can then cook another serving of food.

Embodiments of the splatter lid 10 fulfill the need for a portable and lightweight shield that would prevent the splattering of food 28 onto the interior walls of various sized ovens 12. The use of the present invention would virtually eliminate the time-consuming chore of constant cleaning the inside of ovens 12. The lid may be used at residential homes, commercial cooking establishments, etc.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claim rather than by the foregoing description. All changes which come within the meaning and range of equivalency of the claims are to be embraced within their scope.

Although the figures illustrate shells 14, 20 cooperating together to form a hemispherical shaped barrier 22 with circular shaped apertures 18, 26 therein, one skilled in the art would appreciate that the shells and apertures may be shaped differently to conform to different sized and shaped plates and ovens 12, according to various embodiments. For example, square, rectangular, cubical, etc.

Additionally, although the figures illustrate the protrusion 38 extending outwardly from the front center of shell 20 and being semi-circular shaped, the protrusion may extend outward from anywhere along the shell and be shaped differently, according to various embodiments.

Further, although the figures illustrate four protrusions 36 extending downward from the bottom 42 of the semi-hemispherical barrier members 16, 24 may vary in number, according to various embodiments. For example, three protrusions, five protrusions, six protrusions, etc.

It is also envisioned that the shells 14, 20 forming the dome 22 may be fully and/or partially opaque, according to various embodiments.

It is expected that there could be numerous variations of the design of this invention. An example is that the shells 14, 20; barrier members 16, 24; dome 22; protrusions 36, 38; apertures 18, 26; flange 40 and/or array 46 may vary in width, length, size, diameter, thickness, design, etc., according to alternative embodiments.

Finally, it is envisioned that the components of the device may be constructed of a variety of materials, such as plastic, polymer, and combinations thereof.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A spatter guard for covering food in an oven, comprising:
   a) a first shell configured to cover food, including:
      a1) a first semi-hemispherical barrier member; and
      a2) a first plurality of apertures though the first semi-hemispherical barrier member; and
   b) a second transparent shell pivotally coupled to the first shell wherein the first and second shells together substantially form a hemispherical barrier when in a first position and form an array of substantially parallel semi-hemispherical barriers when in a second position, including:
      b1) a second semi-hemispherical barrier member;
      b2) a second plurality of apertures through the second semi-hemispherical barrier member;
      b3) an outwardly extending protrusion extending from a front of the second shell and configured to be used as a handle for actuating the second shell between the first and second positions; and
      b4) a plurality of downwardly extending protrusions extending downwardly directly from a bottom of the second semi-hemispherical barrier member, the downwardly extending protrusions configured to space the second shell from a surface when in use.

2. The spatter guard of claim 1, wherein the first shell further includes a flange extending outwardly from a bottom of the first hemispherical barrier member.

3. A spatter guard for covering food in an oven, consisting essentially of:
   a) a first shell configured to cover food, including:
      a1) a first semi-hemispherical barrier member; and
      a2) a first plurality of apertures through the first semi-hemispherical barrier member; and b) a second transparent shell pivotally coupled to the first shell where the first and second shells together substantially form a hemispherical barrier when in a first position and form an array of substantially parallel semi-hemispherical barriers when in a second position, including:

b1) a second semi-hemispherical barrier member;

b2) a second plurality of apertures though the second semi-hemispherical barrier member; and b3) an outwardly extending protrusion extending outwardly from a front of the second shell and configured to be used as a handle for actuating the second shell between the first and second positions.

4. The spatter guard of claim 3, wherein the first shell further includes a plurality of downwardly extending protrusions extending downwardly directly from a bottom of the second semi-hemispherical barrier member, the downwardly extending protrusions configured to space the second shell from a surface when in use.

5. The spatter guard of claim 4, wherein the first shell further includes a flange extending outwardly from a bottom of the first hemispherical barrier member.

6. The spatter guard of claim 1, wherein the first shell is transparent.

7. The spatter guard of claim 3, wherein the first shell is transparent.

8. A spatter guard for covering food in an oven, comprising:

a) a first shell configured to cover food, including:

a1) a first semi-hemispherical barrier member; and a2) a first plurality of apertures through the first semi-hemispherical barrier member; and b) a second shell pivotally coupled to the first shell wherein the first and second shells together substantially form a hemispherical barrier when in a first position and form an array of substantially parallel semi-hemispherical barriers when in a second position, including:

b1) a second semi-hemispherical barrier member;

b2) a second plurality of apertures through the second semi-hemispherical barrier member; and b3) a plurality of downwardly extending protrusions extending downwardly directly from a bottom of the second semi-hemispherical barrier member and is configured to space the second shell from a surface when in use.

9. The spatter guard of claim 8, wherein the first shell further includes an outwardly extending protrusion extending from a front of the second shell and configured to be used as a handle for actuating the second shell between the first and second positions.

10. The spatter guard of claim 8, wherein the first shell further includes a flange extending outwardly from a bottom of the first hemispherical barrier member.

11. The spatter guard of claim 8, wherein the second shell is transparent.

* * * * *